United States Patent
Wan et al.

(10) Patent No.: US 11,187,653 B2
(45) Date of Patent: Nov. 30, 2021

(54) INFRARED SENSOR AND INFRARED GAS DETECTOR

(71) Applicant: HANGZHOU SANHUA RESEARCH INSTITUTE CO., LTD., Hangzhou (CN)

(72) Inventors: Xia Wan, Hangzhou (CN); Xinkai Lu, Hangzhou (CN); Huanhuan Rao, Hangzhou (CN); Chengyu Wu, Hangzhou (CN); Longzhong Huang, Hangzhou (CN); Bin Yin, Hangzhou (CN); Lin-Jie Huang, East Amherst, NY (US)

(73) Assignee: HANGZHOU SANHUA RESEARCH INSTITUTE CO., LTD., Hangzhou (CN)

( * ) Notice: Subject to any disclaimer, the term of this patent is extended or adjusted under 35 U.S.C. 154(b) by 0 days.

(21) Appl. No.: 17/044,315

(22) PCT Filed: Jun. 26, 2019

(86) PCT No.: PCT/CN2019/092986
§ 371 (c)(1),
(2) Date: Sep. 30, 2020

(87) PCT Pub. No.: WO2020/001471
PCT Pub. Date: Jan. 2, 2020

(65) Prior Publication Data
US 2021/0156795 A1    May 27, 2021

(30) Foreign Application Priority Data

Jun. 26, 2018 (CN) .......................... 201810669021.0
Jun. 26, 2018 (CN) .......................... 201810669036.7

(Continued)

(51) Int. Cl.
*G01N 21/3504* (2014.01)
*G01N 21/359* (2014.01)
(Continued)

(52) U.S. Cl.
CPC ....... *G01N 21/3504* (2013.01); *G01N 21/359* (2013.01); *G01N 33/004* (2013.01); *B60H 1/008* (2013.01)

(58) Field of Classification Search
CPC ..... G01N 21/359; G01N 33/004; B60H 1/008
See application file for complete search history.

(56) References Cited

U.S. PATENT DOCUMENTS

2004/0201009 A1   10/2004  Hsu et al.
2014/0319357 A1   10/2014  Ogawa et al.
(Continued)

FOREIGN PATENT DOCUMENTS

CN        1034433 A       8/1989
CN      101303298 A      11/2008
(Continued)

OTHER PUBLICATIONS

Xiaohong An, Fangze Liu, Yung Joon Jung, Swastik Kar, "Tunable Graphene-Silicon Heterojunctions for Ultrasensitive Photodetection", Nano Letters, Jan. 25, 2013, pp. 909-916, vol. 13, No. 3, American Chemical Society.

*Primary Examiner* — David P Porta
*Assistant Examiner* — Meenakshi S Sahu
(74) *Attorney, Agent, or Firm* — Cheng-Ju Chiang

(57) ABSTRACT

The present disclosure discloses an infrared sensor, an infrared gas detector and an air quality detection device. The infrared sensor includes electrodes, a substrate, an isolation layer and a graphene film. The graphene film has a periodical nanostructure. The infrared sensor enhances the absorption of infrared light, and is capable of only absorbing specific infrared wavelengths, thus improving the selective performance of the infrared gas detector.

20 Claims, 8 Drawing Sheets

(30) Foreign Application Priority Data

| Jun. 26, 2018 | (CN) | 201810670505.7 |
| Jun. 26, 2018 | (CN) | 201810670530.5 |
| Jun. 26, 2018 | (CN) | 201810670537.7 |
| Jun. 26, 2018 | (CN) | 201810670548.5 |
| Jun. 26, 2018 | (CN) | 201810671851.7 |
| Jun. 26, 2018 | (CN) | 201810671852.1 |
| Jun. 26, 2018 | (CN) | 201810671853.6 |
| Jun. 26, 2018 | (CN) | 201810671861.0 |

(51) Int. Cl.
*G01N 33/00* (2006.01)
*B60H 1/00* (2006.01)

(56) References Cited

U.S. PATENT DOCUMENTS

| 2018/0006067 | A1 | 1/2018 | Ogawa et al. |
| 2018/0106933 | A1 | 4/2018 | Chanda et al. |
| 2018/0178613 | A1* | 6/2018 | Zhang .................. B60H 1/008 |

FOREIGN PATENT DOCUMENTS

| CN | 201653956 U | | 11/2010 |
| CN | 103715291 A | | 4/2014 |
| CN | 103822893 A | | 5/2014 |
| CN | 103823438 A | | 5/2014 |
| CN | 104280357 | * | 5/2014 |
| CN | 104280357 A | | 1/2015 |
| CN | 104280358 A | | 1/2015 |
| CN | 204086116 U | | 1/2015 |
| CN | 104807771 A | | 7/2015 |
| CN | 105115928 A | | 12/2015 |
| CN | 204821422 U | | 12/2015 |
| CN | 105548074 A | | 5/2016 |
| CN | 105679857 | * | 6/2016 |
| CN | 105679857 A | | 6/2016 |
| CN | 106169516 A | | 11/2016 |
| CN | 105355702 B | | 4/2017 |
| CN | 106601857 | * | 4/2017 |
| CN | 106601857 A | | 4/2017 |
| CN | 106784122 A | | 5/2017 |
| CN | 106793733 A | | 5/2017 |
| CN | 107479296 A | | 12/2017 |
| CN | 107728342 A | | 2/2018 |
| CN | 207096098 U | | 3/2018 |
| CN | 108107609 A | | 6/2018 |

* cited by examiner

INFRARED SENSOR AND INFRARED GAS DETECTOR

CROSS REFERENCE TO RELATED APPLICATIONS

The present application is a 35 U.S.C. § 371 National Phase conversion of International (PCT) Patent Application No. PCT/CN2019/092986, filed on Jun. 26, 2019, which claims benefit of Chinese Application No. 201810670530.5, filed on Jun. 26, 2018, Chinese Application No. 201810670537.7, filed on Jun. 26, 2018, Chinese Application No. 201810669021.0, filed on Jun. 26, 2018, Chinese Application No. 201810671853.6, filed on Jun. 26, 2018, Chinese Application No. 201810670505.7, filed on Jun. 26, 2018, Chinese Application No. 201810670548.5, filed on Jun. 26, 2018, Chinese Application No. 201810669036.7, filed on Jun. 26, 2018, Chinese Application No. 201810671861.0, filed on Jun. 26, 2018, Chinese Application No. 201810671852.1, filed on Jun. 26, 2018, Chinese Application No. 201810671851.7, filed on Jun. 26, 2018, the disclosure of which is incorporated by reference herein. The PCT International Patent Application was filed and published in Chinese.

TECHNICAL FIELD

The present application relates to a field of photoelectric detection technology, in particular to an infrared sensor and an infrared gas detector having the infrared sensor.

BACKGROUND

A gas sensor is a gas sensing device which is based on selection absorption characteristics of near-infrared spectra of different gas molecules, and uses the relationship between gas concentration and absorption intensity to identify gas components and determine its concentration. In related technologies, graphene/silicon photodetectors are photoelectric effect infrared photodetectors in which graphene films are combined with silicon substrates to form graphene/silicon Schottky junction. The photo-generated carriers generated by the incident infrared light waves and absorbed by the graphene films are quickly separated by the graphene/silicon Schottky to form a photo-generated current.

The graphene phototransistor is an infrared photodetector of the photoelectric effect, which includes a source electrode, a drain electrode and a gate electrode. When a voltage is applied between the source electrode and the drain electrode without light, a dark current is generated in the graphene film. The photo-generated carriers generated by the incident infrared light waves absorbed by the graphene films are separated by an electric field between the source electrode and the drain electrode to form the photo-generated current.

However, the existing graphene/silicon photodetectors and graphene phototransistors can only achieve broad spectrum absorption, but cannot only absorb light waves of characteristic wavelengths, which reduces the selective performance of the detector.

SUMMARY

To this end, one aspect of the present application provides an infrared sensor which enhances the absorption of infrared light. The infrared sensor is capable of absorbing only specific infrared wavelengths, which improves the performance of a detector.

Another aspect of the present application also provides an infrared gas detector.

The infrared sensor according to embodiments of a first aspect of the present application includes: a first electrode; a substrate which is provided on an upper surface of the first electrode; an isolation layer which is provided on an upper surface of the substrate; a second electrode which is provided on an upper surface of the isolation layer; and a graphene film which is covered on the second electrode. The graphene film has periodic nanostructures.

According to the infrared sensor of the embodiments of the present application, by arranging periodic nanostructures on the graphene film, the absorption of infrared light is enhanced and only specific infrared wavelengths can be absorbed, thereby improving the performance of the detector.

In some embodiments, the isolation layer is provided with a first window and a first inner side surface surrounding the first window, and the first window is used to expose part of the upper surface of the substrate. The second electrode is provided with a second window and a second inner side surface surrounding the second window. The first window and the second window are arranged correspondingly. The graphene film is covered on part of the upper surface of the substrate, the first inner side surface of the isolation layer, the second inner side surface of the second electrode and the upper surface of the second electrode.

In some embodiments, there are a plurality of the first windows which are evenly spaced. There are a plurality of the second electrodes and a plurality of the graphene films. An outer periphery of each first window is surrounded by one of the second electrodes, and the upper surface of each second electrode is covered with one of the graphene films.

In some embodiments, the graphene film has the periodic nanostructures on a part of the upper surface of the substrate. A projection of the graphene film on a horizontal plane is located within a projection of the second electrode on the horizontal plane. The graphene film is a doped graphene film or a composite graphene film.

In some embodiments, the infrared sensor further includes a third electrode provided on the upper surface of the isolation layer. The second electrode and the third electrode are spaced apart from each other. The graphene film is covered on the upper surface of the isolation layer between the second electrode and the third electrode, the inner surface of the second electrode opposite to the third electrode, the inner side of the third electrode opposite to the second electrode, at least part of the upper surface of the second electrode and at least part of the upper surface of the third electrode. The periodic nanostructures are provided on a portion of the graphene film on the upper surface of the isolation layer.

In some embodiments, the graphene film includes a first edge and a second edge opposite to each other. The second electrode includes a first side away from the third electrode, the third electrode includes a second side away from the second electrode, the first edge is located inside the first side, and the second edge is located inside the second side In some embodiments, the third electrode and the second electrode are electrically connected.

In some embodiments, the periodic nanostructures are a plurality of hole-like structures or doped structures.

An infrared gas detector according to embodiments of a second aspect of the present application includes a housing, an infrared light source and the infrared sensor according to any of the above embodiments. The housing is provided with a through hole, and the housing includes a first housing and a second housing connected to the first housing. The first housing has a first chamber communicating with the through hole. An inner surface of a side wall of the first housing is provided with a first reflection surface, a second reflection surface, a third reflection surface and a fourth reflection surface. The second housing is provided with a first channel and a second channel spaced apart from each other. The first channel is in communication with the first chamber, and the second channel is in communication with the first chamber. The infrared light source is arranged in the first channel. The infrared sensor is arranged in the second channel. An infrared light emitted by the infrared light source is transmitted to the first reflection surface along the first channel, and is reflected to the fourth reflection surface sequentially via the first reflection surface, the second reflection surface and the third reflection surface. The infrared light incident on the fourth reflection surface is reflected by the fourth reflection surface and is transmitted to the infrared sensor along the second channel. A plane on which an optical path of the infrared light in the first channel and an optical path in the second channel are located is a first plane. A plane where an optical path of the infrared light is reflected to the fourth reflection surface sequentially via the first reflection surface, the second reflection surface and the third reflection surface is a second plane. The second plane and the first plane are perpendicular to each other.

Figure 1:
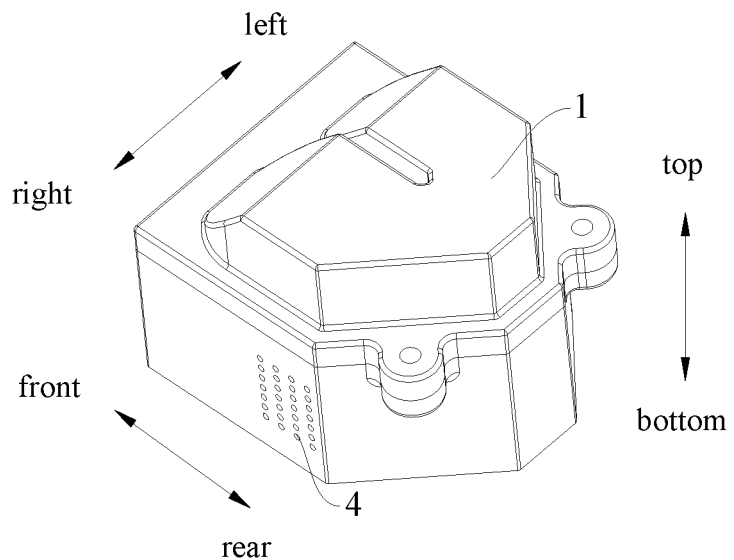
FIG. 1 is an overall structure view of an infrared gas detector according to an embodiment of the present application.

REFERENCE SIGNS infrared gas detector 100, housing 1, first housing 11, first chamber 110, first side wall 111, second side wall 112, third side wall 113, fourth side wall 114, fifth side wall 115, sixth side wall 116, second housing 12, second chamber 120, first channel 121, first section 1211, second section 1212, third section 1213, second channel 122, second left side wall 123, second right side wall 124, infrared light source 2, infrared sensor 3, first electrode 31, substrate 32, part of the upper surface 321 of the substrate, isolation layer 33, first window 330, part of the upper surface 331 of the isolation layer, first inner side surface 332, second electrode 34, second window 341, third electrode 35, graphene film 36, periodic nanostructure 361, through hole 4, first through hole 41, second through hole 42, first reflection surface 5, second reflection surface 6, third reflection surface 7, fourth reflection surface 8, circuit board 9, reflector cup 10, cylindrical section 101, parabolic section 102, second processor 1001, signal processing circuit 1002, first processor 200, display 300, voltage conversion module 400, warning device 500.

DETAILED DESCRIPTION

The embodiments of the application are described in detail below, and examples of the embodiments are shown in accompanying drawings. The embodiments described below with reference to the drawings are exemplary, and are intended to explain the application, and should not be understood as a limitation to the present application. In the description of the present application, it should be understood that the orientation or positional relationship indicated by the terms "center", "lateral", "length", "width", "upper", "lower", "inner", "outer", "circumferential" and so on are based on the orientation or positional relationship shown in the drawings, which is only for the convenience of describing the present application and simplifying the description, and does not indicate or imply that the device or element referred to must have a specific orientation, be constructed and operated in a specific orientation, and therefore cannot be understood as a restriction to the present application. Moreover, the terms "first" and "second" are only used for descriptive purposes, and cannot be understood as indicating or implying relative importance or implicitly indicating the number of technical features. Therefore, the features defined with "first" and "second" may explicitly or implicitly include at least one of the features.

An infrared sensor and an infrared gas detector according to the embodiments of the present application are described below with reference to the drawings.

As shown in FIGS. 1 to 9, the infrared gas detector according to the embodiments of the present application includes a housing 1, an infrared light source 2 and an infrared sensor 3, wherein the housing 1 is provided with a through hole 4. In the present application, unless expressly stipulated and defined otherwise, a first feature located "above" or "below" a second feature may be in condition that the first feature and the second feature are in direct contact or in indirect contact.

The housing 1 includes a first housing 11 and a second housing 12. In the present application, the terms "first" and "second" are only used for descriptive purposes, and cannot be understood as indicating or implying relative importance or implicitly indicating the number of indicated technical features. Therefore, the features defined with "first" and "second" may explicitly or implicitly include at least one of the features.

Figure 2:
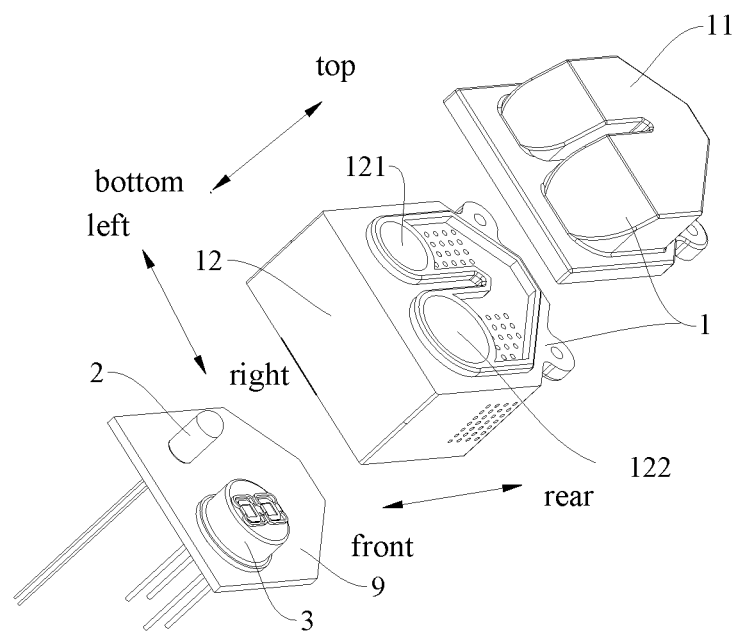
FIG. 2 is an exploded view of the infrared gas detector according to an embodiment of the present application.
Figure 3:
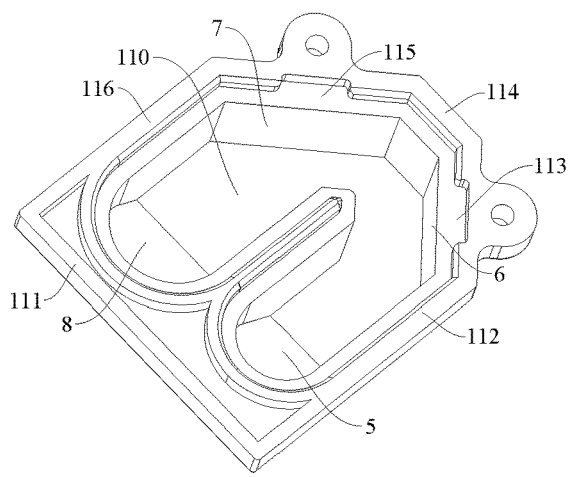
FIG. 3 is a bottom view of a first housing of the infrared gas detector according to the embodiment of the present application.
Figure 4:
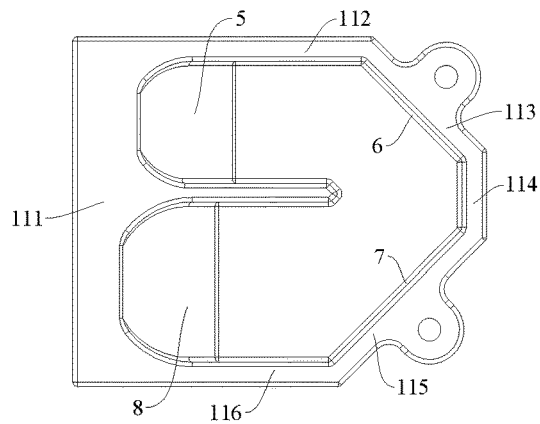
FIG. 4 is a structural view with a bottom of the first housing of the infrared gas detector facing upwardly according to an embodiment of the present application.
Figure 5:
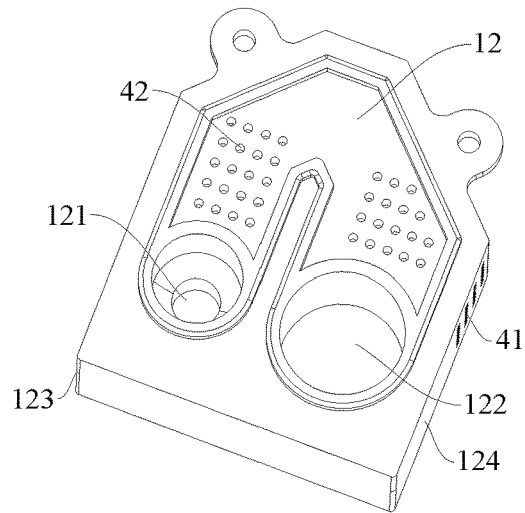
FIG. 5 is a structural view of a second housing of the infrared gas detector according to an embodiment of the present application.

As shown in FIGS. 2, 3 and 4, the first housing 11 includes a first chamber 110 which is in communication with the through hole 4. Gas to be measured can enter the first chamber 110 through the through hole 4. An inner surface of a side wall of the first housing 11 is provided with a first reflection surface 5, a second reflection surface 6, a third reflection surface 7 and a fourth reflection surface 8. That is, a first reflection surface 5, a second reflection surface 6, a third reflection surface 7 and a fourth reflection surface 8 are provided on the side wall surface surrounding the first chamber 110. As shown in FIGS. 1, 2, and 5, the second housing 12 is connected to the first housing 11. The second housing 12 is provided with a first channel 121 and a second channel 122 arranged at intervals. The first channel 121 is in communication with the first chamber 110, and the second channel 122 is in communication with the first chamber 110. The infrared light source 2 is arranged in the first channel 121, and the infrared sensor 3 is arranged in the second channel 122. Infrared light emitted by the infrared light source 2 is transmitted to the first reflection surface 5 along the first channel 121, and is sequentially reflected to the fourth reflection surface 8 via the first reflection surface 5, the second reflection surface 6 and the third reflection surface 7. The infrared light incident on the fourth reflection surface 8 is reflected by the fourth reflection surface 8 and transmitted to the infrared sensor 3 along the second channel 122. A plane where an optical path of the infrared light in the first channel 121 and an optical path in the second channel 122 are located is the first plane. It can be understood that limiting the transmission of the infrared light in the first plane to the first channel 121 and the second channel 122 can improve reception rate of light beam. A plane where the infrared light starts from the first reflection surface 5 to the second reflection surface 6 and the third reflection surface 7 and then reflects to the fourth reflection surface 8 is a second plane. The second plane and the first plane are perpendicular to each other.

Figure 7:
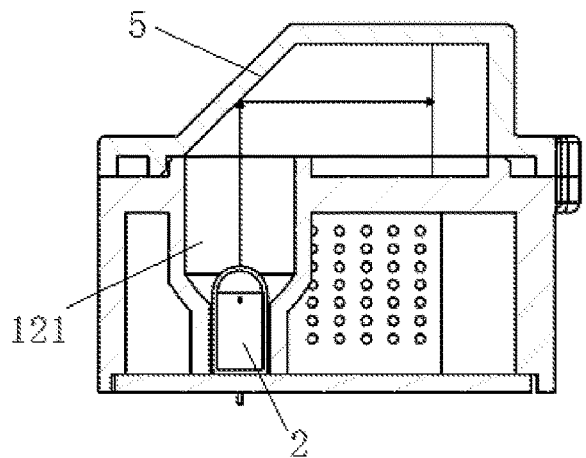
FIGS. 7 to 9 are schematic views of infrared light transmission of the infrared gas detector according to an embodiment of the present application.
Figure 8:
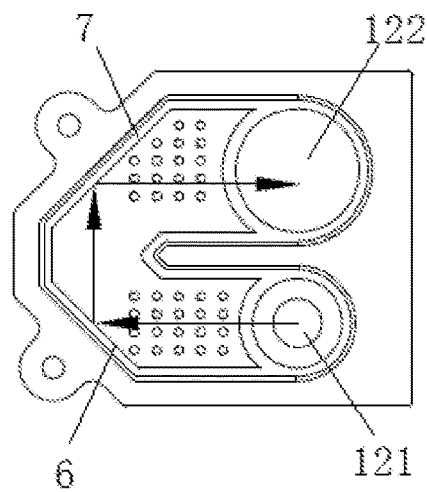
Figure 9:
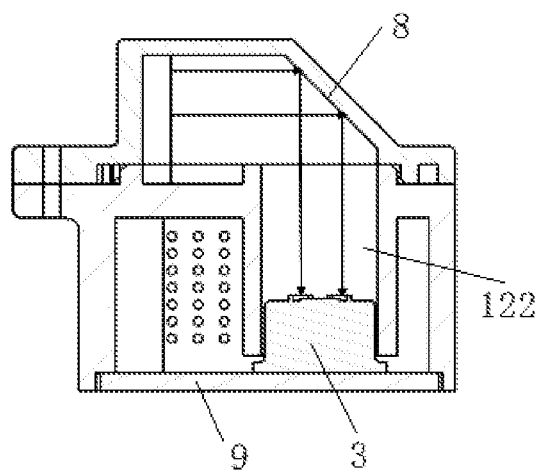

In other words, the transmission paths of the infrared light are that the infrared light of the infrared light source 2 is transmitted to the first reflection surface 5 along the first channel 121 and reflected to the second reflection surface 6 via the first reflection surface 5 (as shown in FIG. 7). The infrared light incident on the second reflection surface 6 is reflected by the second reflection surface 6 to the third reflection surface 7. The infrared light incident on the third reflection surface 7 is reflected by the third reflection surface 7 to the fourth reflection surface 8 (as shown in FIG. 8). The infrared light incident on the fourth reflection surface 8 is reflected by the fourth reflection surface 8 and transmitted to the infrared sensor 3 along the second channel 122 (as shown in FIG. 9). A plane where the infrared light is transmitted in the first channel 121 and the second channel 122 is perpendicular to a plan where the infrared light is reflected after being emitted from the first reflection surface 5 to the second reflection surface 6, the third reflection surface 7 and then reaches the fourth reflection surface 8. That is, the infrared light is transmitted in two planes.

Specifically, material of the housing 1 is brass, aluminum alloy, plastic or glass etc. The infrared light source 2 may be an infrared light generated by heating and luminescence of the filament, or an infrared LED light source. It is understood that the configuration of the infrared light source 2 is not limited to this according to the present application.

According to the infrared gas detector of the embodiment of the present application, by transmitting the infrared light in two planes perpendicular to each other, making full use of the space of the infrared gas detector, it is possible to realize beam transmission with a large optical path in a smaller space. Therefore, the volume of the infrared gas detector can be reduced.

In some embodiments, as shown in FIGS. 3 and 4, the side wall of the first housing 11 includes a first side wall 111, a second side wall 112, a third side wall 113, a fourth side wall 114, a fifth side wall 115 and a sixth side wall 116 which are connected in sequence and enclose the first chamber 110. The inner surface of the first side wall 111 is outwardly inclined by 45° along a direction toward the second housing 12. The second side wall 112 and the sixth side wall 116 are parallel to each other. An angle between the third side wall 113 and the fourth side wall 114 is 45°, an angle between the fifth side wall 115 and the fourth side wall 114 is 45°, and an angle between the third side wall 113 and the fifth side wall 115 is 90°. The first reflection surface 5 and the fourth reflection surface 8 are provided on the inner surface of the first side wall 111 and are spaced apart from each other. The second reflection surface 6 is provided on an inner surface of the third side wall 113. The third reflection surface 7 is provided on an inner surface of the fifth side wall 115. Here, a direction toward the first chamber 110 is defined as an inward direction, and a direction away from the first chamber 110 is defined as an outward direction.

In other words, an outer peripheral profile of a cross section of the first housing 11 is substantially hexagonal. The first chamber 110 of the first housing 11 is surrounded by the first side wall 111, the second side wall 112, the third side wall 113, the fourth side wall 114, the fifth side wall 115 and the sixth side wall 116. The second side wall 112 and the sixth side wall 116 are parallel to each other and spaced apart from each other. The inner surface of the first side wall 111 is inclined by 45° from inside to outside along a direction from the first housing 11 to the second housing 12. Both of the third side wall 113 and the fifth side wall 115 are inclined by 45° with respect to the fourth side wall 114, and the angle between the third side wall 113 and the fifth side wall 115 is 90°. The first reflection surface 5 and the fourth reflection surface 8 are provided on the inner surface of the first side wall 111 and are spaced apart from each other. That is, both of the first reflection surface 5 and the fourth reflection surface 8 are inclined at 45° from the inside to the outside along the direction from the first housing 11 to the second housing 12. As a result, the first reflection surface 5 receives the infrared light in the first channel 121 and reflects it to the second reflection surface 6. The light incident on the fourth reflection surface 8 is reflected to the infrared sensor 3 along the second channel 122. The second reflection surface 6 is provided on the inner surface of the third side wall 113, and the third reflection surface 7 is provided on the inner surface of the fifth side wall 115. That is, an angle between the second reflection surface 6 and the fourth side wall 114 is 45°, an angle between the third reflection surface 7 and the fourth side wall 114 is 45°, and an angle between the second reflection surface 6 and the third reflection surface 7 is 90°. In this way, the light incident on the first reflection surface 5 is sequentially reflected on the fourth reflection surface 8 via the second reflection surface 6 and the third reflection surface 7.

Specifically, the fourth side wall 114 is perpendicular to the second side wall 112 and also perpendicular to the sixth side wall 116. The length of the fourth side wall 114 is smaller than the distance between the second side wall 112 and the sixth side wall 116. An included angle between the inner surface of the fourth side wall 114 and the inner surface of the third side wall 113 is 135°. An included angle between the inner surface of the fourth side wall 114 and the inner surface of the fifth side wall 115 is 135°. More specifically, the inner surface of the first side wall 111 includes a first inner surface and a second inner surface. The first inner surface and the second inner surface are spaced apart from each other, and the first inner surface is located inside the second inner surface. The first reflection surface 5 is provided on the first inner surface, and the fourth reflection surface 8 is provided on the second inner surface. That is, the first reflection surface 5 is located inside the fourth reflection surface 8.

In some embodiments, as shown in FIG. 5, axial directions of the first channel 121 and the second channel 122 are parallel. It can be understood that the axial parallelism of the first channel 121 and the axial parallelism of the second channel 122 are within an error allowed in the art.

In some embodiments, the second housing 12 is provided below the first housing 11. Both the first channel 121 and the second channel 122 are extended downwardly from an upper surface of a top wall of the second housing 12 and extend to a bottom of the second housing 12. In other words, the first housing 11 and the second housing 12 are arranged in sequence from a top-to-bottom direction and connected to each other. The first channel 121 and the second channel 122 both extend downwardly and extend from the upper surface of the second housing 12 to the bottom of the second housing 12.

Figure 6:
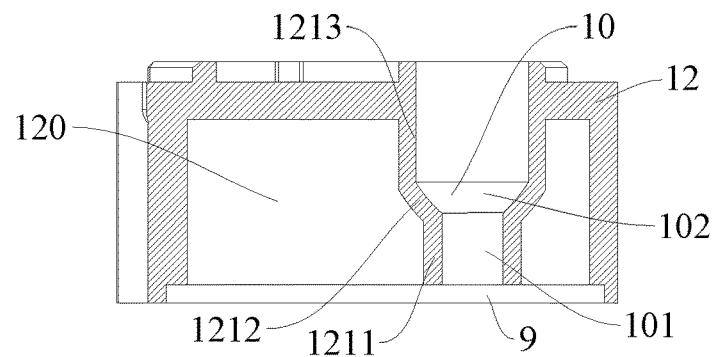
FIG. 6 is a cross-sectional view of the second housing of the infrared gas detector according to an embodiment of the present application.

In some embodiments, as shown in FIGS. 2, 5 and 6, the infrared gas detector further includes a circuit board 9. The bottom of the second housing 12 is provided with an opening, that is, the bottom of the second housing 12 is opened, so that the circuit board 9 can be installed inside the second housing 12. Both the infrared light source 2 and the infrared sensor 3 are arranged on an upper surface of the circuit board 9. In other words, the infrared light source 2 is provided on the upper surface of the circuit board 9 and located in the first channel 121. Alternatively, the infrared light source 2 is arranged at a bottom end of the first channel 121. The infrared sensor 3 is provided on the upper surface of the circuit board 9. Alternatively, the infrared sensor 3 is arranged at a bottom end of the second channel 122.

Specifically, the circuit board 9 is provided with a signal processing circuit, which can obtain real-time data value of the infrared sensor 3 and perform filtering, amplifying, temperature compensation and digital-to-analog conversion on a voltage signal generated by the infrared sensor 3. The signal processing circuit can also modulate the infrared light source 2 in a pulse mode, so that the infrared light source 2 emits light periodically.

In some embodiments, the second housing 12 includes a second chamber 120 communicating with the first chamber 110. The through hole 4 is provided on the second housing 12. The through hole 4 includes a first through hole 41 and a second through hole 42. The first through hole 41 is disposed on the side wall of the second housing 12 so as to communicate with the second chamber 120. The second through hole 42 is provided on the top wall of the second housing 12 so as to communicate the second chamber 120 and the first chamber 110. Gas to be measured enters the second chamber 120 through the first through hole 41, and the gas in the second chamber 120 enters the first chamber 110 through the second through hole 42.

It is understandable that the through hole 4 is provided on the second housing 12 so that the gas enters the first chamber 110 of the first housing 11 through the second chamber 120 of the second housing 12, and the first housing 11 is not provided with a through hole communicating with the first chamber 110, thereby, it can reduce the leakage of the infrared light during the transmission process in the first housing 11, improve the utilization rate of the light source and the receiving rate of the infrared detector, thereby improving detection efficiency. Of course, in other embodiments, the first housing 11 is provided with the through hole 4.

Specifically, the first through hole 41 is provided on the side wall of the second housing 12 and the second through hole 42 is provided on the top wall of the second housing 12. Furthermore, there are a plurality of first through holes 41 and a plurality of second through holes 42. In other words, the side wall of the second housing 12 is provided with the plurality of the first through holes 41, and the top wall of the second housing 12 is provided with the plurality of second through holes 42 in order to improve air intake efficiency. In the description of the present application, "a plurality of" means at least two, such as two, three, etc., unless otherwise specifically defined.

In some embodiments, as shown in FIGS. 2 and 5, the side wall of the second housing 12 includes a second left side wall 123 and a second right side wall 124. The second right side wall 124 and the second left side wall 123 are spaced apart from each other, and the first through holes 41 are provided on the second left side wall 123 and the second right side wall 124. In other words, both the second left side wall 123 and the second right side wall 124 are provided with the first through holes 41. Specifically, the second left side wall 123 is provided with the plurality of first through holes 41, and/or the second right wall 124 is provided with the plurality of first through holes 41.

A partition is provided in the second chamber 120 to divide the second chamber 120 into a second left chamber and a second right chamber. The first through hole 41 on the second left side wall 123 communicates with the second left chamber, and the first through hole 41 on the second right side wall 124 communicates with the second right chamber. It is understandable that the second chamber 120 is separated by the partition in order to prevent the gas which enters the second chamber 120 via the first through hole 41 of the second left side wall 123 from leaking out via the first through hole 41 of the second right side wall 124, and prevent the gas which enters the second chamber 120 via the first through hole 41 of the second right side wall 124 from leaking out via the first through hole 41 of the second left side wall 123. Therefore, it is avoided that the gas to be measured cannot enter the first chamber 110 from the second chamber 120.

In some embodiments, as shown in FIG. 6, the infrared gas detector further includes a reflector cup 10 which is nested in the first channel 121 and is close to the inner surface of the first channel 121. The infrared light source 3 is arranged in the reflector cup 10. Specifically, the reflector cup 10 is nested at a bottom end of the first channel 121. The reflector cup is a kind of reflector which is to use limited light energy to control illumination distance and area of main spot through the light reflector.

In some alternative embodiments, the reflector cup 10 includes a cylindrical section 101 and a parabolic section 102. The parabolic section 102 is connected to an upper end of the cylindrical section 101. Specifically, an inner diameter of the cylindrical section 101 is consistent along an axial direction of the first channel 121. That is, the inner diameter of the cylindrical section 101 remains the same along the axial direction of the first channel 121.

The first channel 121 includes a first section 1211, a second section 1212 and a third section 1213 which are connected in sequence along a bottom-to-top direction. An outer peripheral profile of the cylindrical section 101 is adapted to an inner peripheral profile of the first section 1211. An outer peripheral profile of the parabolic section 102 is adapted to an inner peripheral profile of the second section 1212. An inner diameter of the third section 1213 is constant along the axial direction of the first channel 121. That is, the inner diameter of the third section 1213 remains the same along the axial direction of the first channel 121.

The reflector cup 10 having above structure is suitable for an infrared light source produced by heating and emitting light by a filament with a certain height. This structure can facilitate placing the light-emitting surface of the filament on a focal plane of a parabolic reflection surface of the parabolic section 102. It can be understood that the structure of the reflector cup 10 is not limited to this. For example, in other alternative embodiments, the whole reflector cup 10 is formed as the parabolic reflection surface. The reflector cup 10 of this structure is suitable for thinner infrared LED light sources.

In some embodiments, the inner surface of the side wall of the first housing 11 is coated with a gold film to form the first reflection surface 5, the second reflection surface 6, the third reflection surface 7 and the fourth reflection surface 8. In other words, the reflection surface is formed by a gold-coated film on the inner surface of the side wall of the first housing 11. Specifically, the inner surface of the side wall of the first housing 11 is polished before the gold film is coated, which is beneficial to total reflection of light, reduces loss and also avoid material oxidation.

The infrared sensor according to an embodiment of the present application is described below with reference to FIGS. 10 to 12.

Figure 10:
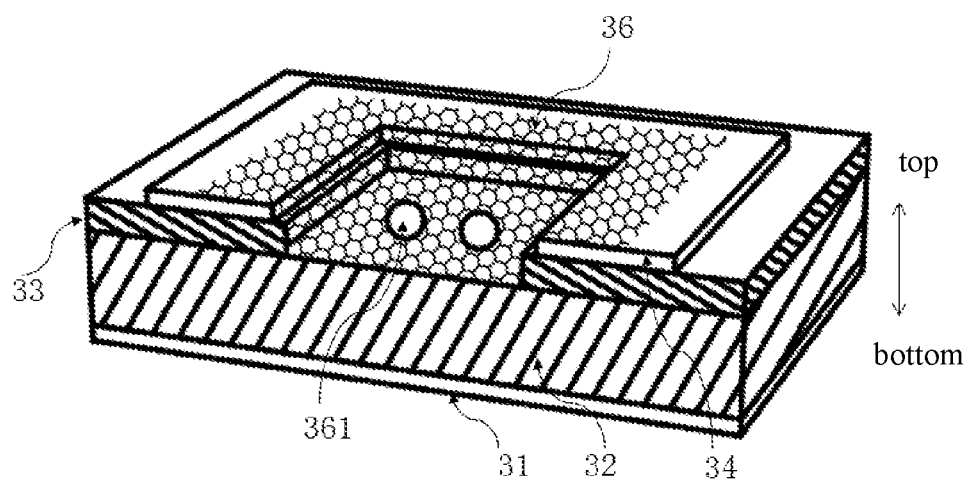
FIG. 10 is a cross-sectional view of an infrared sensor according to an embodiment of the application.
Figure 11:
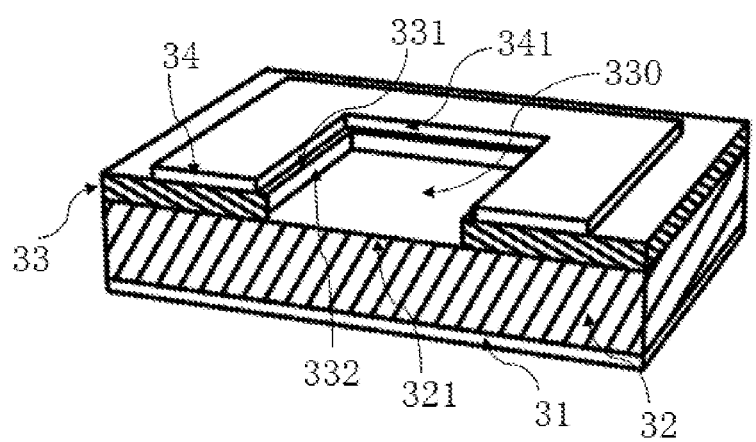
FIG. 11 is a cross-sectional view of the infrared sensor uncovered with a graphene film according to an embodiment of the application.
Figure 12:
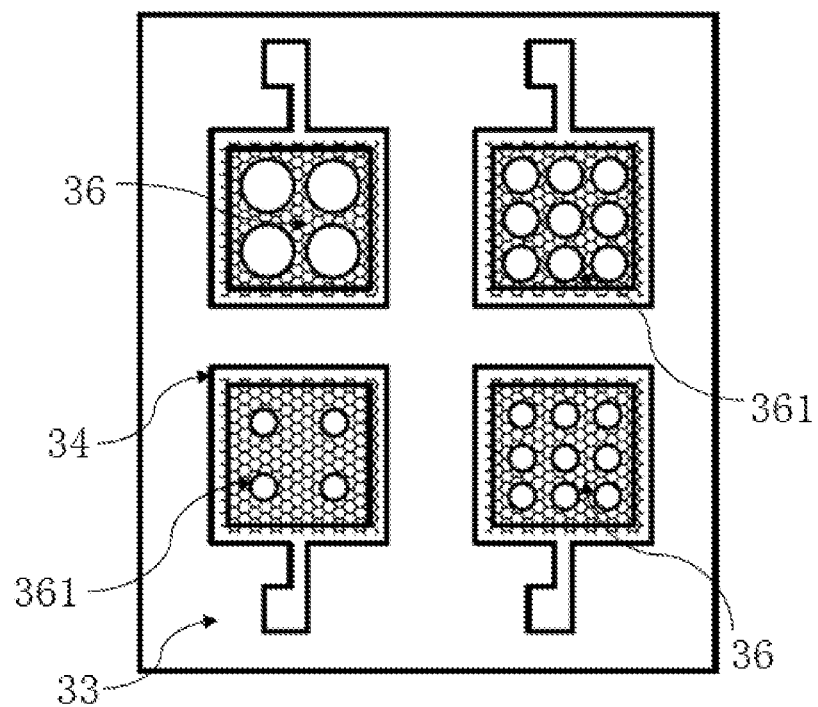
FIG. 12 is a top view of the infrared sensor according to an embodiment of the application.

As shown in FIGS. 10 to 12, the infrared sensor 3 according to the embodiment of the application includes a first electrode 31, a substrate 32, an isolation layer 33, a second electrode 34 and a graphene film 36. The substrate 32 is provided on an upper surface of the first electrode 31. Specifically, the material of the substrate 32 is generally silicon in the art, that is, a silicon substrate. Specifically, the silicon substrate includes an N-type or P-type silicon material with a resistivity of 0.1 to 100 $\Omega\cdot cm$. The isolation layer 33 is provided on an upper surface of the substrate 32. Specifically, the isolation layer 33 is a silica isolation layer, and the thickness of the silica isolation layer is 100 nm to 1000 nm. However, the present application is not limited to this, and the material of the isolation layer 33 can be selected by those skilled in the art according to actual needs.

The isolation layer 33 is provided with a first window 330 and a first inner side surface 332 enclosing the first window 330. The first window 330 can expose part of the upper surface 321 of the substrate 32. In other words, the isolation layer 33 is provided with a through hole forming the first window 330, and the first window 330 is enclosed by the first inner side surface 332 of the isolation layer 33, so that part of the upper surface 321 of the substrate 32 and the through hole form a groove structure. Therefore, a bottom wall surface of the groove structure is a part of the upper surface 321 of the substrate 32, and a side wall surface of the groove structure is the first inner side surface 332 of the isolation layer 33.

The second electrode 34 is provided on an upper surface of the isolation layer 33. The second electrode 34 is provided with a second window 341 and a second inner side surface surrounding the second window 341. The second window 341 and the first window 330 are set correspondingly. In other words, the second electrode 34 does not cover the first window 330, but a second window 341 aligned with the first window 330 in a vertical direction is opened on the second electrode 34. Alternatively, the second electrode 34 surrounds an outer periphery of the first window 330. In other words, the second electrode 34 has the second window 341 extending through the second electrode 34 in the vertical direction of the second electrode 34 so that the second electrode 34 has a ring structure. The second window 341 is located above the first window 330 of the isolation layer 33, and the first inner surface 332 of the isolation layer 33 (that is, a sidewall surface of the groove structure) is on the inner surface of the second electrode 34 (that is, a wall surface of the second window 341) to fully expose the first window 330. Therefore, by arranging the second electrode 34 to surround the outer periphery of the first window 330, a circuit can be made more stable and collected signals can be stronger.

It can be understood that the present application is not limited to this. For example, the second electrode 34 does not surround a circumference of the first window 330, but is a part of the first window 330. That is, the second electrode 34 is an unclosed structure, such as the second electrode 34 is generally U-shaped, or the second electrode 34 is located only on one side of the first window 330.

Alternatively, an outer surface of the second electrode 34 is located inside an outer surface of the isolation layer 33. That is, the second electrode 34 is located in an area surrounded by a boundary of the isolation layer 33. Furthermore, the shape of the second window 341 is the same as the shape of the first window 330. That is, two cross sections (planes perpendicular to a top-to-bottom direction) of the first window 330 and the second window 341 are the same, and a cross-sectional area of the second window 341 is greater than or equal to that of the first window 330 in order to expose the first window 330. Furthermore, a center line of the second window 341 and a center line of the first window 330 may be overlapped. For example, as shown in FIG. 10, the cross sections of the second window 341 and the first window 330 are both square. The second window 341 is located directly above the first window 330. That is, the center line of the second window 341 and the center line of the first window 330 are overlapped. The widths of the second windows 341 having a through-hole squared configuration are larger than the widths of the first windows 330. Shapes of the second window 341 and the first window 330 are not limited to this in the present application. For example, the cross sections of the second window 341 and the first window 330 may both be rectangular. The length of the through hole is greater than the length of the first window 330. The width of the through hole is greater than the width of the first window 330. It can be understood that the cross sections of the first window 330 and the second window 341 may be triangular, diamond, circular, etc., in addition to being square.

The graphene film 36 is covered on a portion of the upper surface 321 of the substrate 32, the first inner side surface 332 of the isolation layer 33 (the wall surface of the first window 330), a second inner side surface of the second electrode 34 (the wall surface of the second window 341), and an upper surface of the second electrode 34. In other words, the graphene film 36 is laid on positions of the second window 341 and the first window 330. That is, the graphene film 36 is sequentially attached to the upper surface of the second electrode 34, the second inner surface of the second electrode 34, the first inner side surface 332 of the isolation layer 33 and a portion of the upper surface 321 of the substrate 32. More specifically, a cross-sectional area of the graphene film 36 is larger than a cross-sectional area of the second window 341 so that the boundary of the graphene film 36 is located on the upper surface of the second electrode 34.

It can be understood that the graphene film 36 is not only a filter capable of absorbing characteristic wavelengths, but also an active film. Because graphene has metallic properties, it can be combined with a silicon substrate to form a Schottky junction. The photo-generated carriers generated by the characteristic infrared light waves absorbed by the graphene film 36 are quickly separated by the Schottky junction to form a photo-generated current. The infrared sensor according to the embodiment of the present application has advantages of fast response time and not being affected by external heat sources.

The graphene film 36 on a part of the upper surface 321 of the substrate 32 is provided with periodic nanostructures 361. In other words, a portion of the graphene film 36 on the upper surface 321 of the substrate 32 is provided with the periodic nanostructures 361. Alternatively, the periodic nanostructures 361 are a plurality of hole-like structures, and a cross-section of the hole-like structure is in the shape of a circle, a square, a diamond or a triangle. For example, as shown in FIG. 10, the cross-section of the hole-like structure is circular. But, the cross-sectional shape of the hole-like structure is not limited to this in this application, and those skilled in the art can make selections according to actual needs. In the description of the application, "a plurality of" means at least two, such as two, three, etc., unless specifically defined otherwise.

It can be understood that the present application is not limited to this. For example, the periodic nanostructures 361 include a plurality of doping treatment structures. In other words, the periodic nanostructure can be obtained by doping the graphene film 36.

It can be understood that the infrared sensor 3 in the embodiment of the present application does not need to apply an additional external voltage. The graphene film 36 provided with the periodic nanostructures 361 is used as a filter, which can enhance the absorption of infrared light and only absorb specific infrared wavelengths to detect specific gases. Therefore, the selection performance of the detector is improved, the volume of the infrared sensor can be reduced, and the preparation and cost are easy.

Alternatively, the first electrode 31, the substrate 32, the isolation layer 33 and the second electrode 34 are sequentially arranged along a bottom-to-top direction. It can be understood that in the art, the first electrode 31 is generally referred to as a bottom electrode which can form an ohmic contact with the substrate 32. The first electrode 31 is a metal thin film electrode, and its metal material is gallium indium alloy, titanium alloy or aluminum. The second electrode 34 is generally called a top electrode. The second electrode 34 is a metal thin film electrode of which the metal material is aluminum, gold, or gold-chromium alloy.

Alternatively, when a side wall surface of the second window 341 of the second electrode 34 is located outside of the side wall surface of the first window 330, a part of the upper surface 331 of the isolation layer 33 around the first window 330 is exposed. The graphene film 36 is also covered on part of the upper surface 331 of the isolation layer 33. That is, the graphene film 36 is covered on a part of the upper surface 321 of the substrate 32, the first inner side 332 of the isolation layer 33 (the side wall surface of the first window 330), a portion of the upper surface 331 of the isolation layer 33, the second inner side surface of the second electrode 34 (the side wall surface of the second window 341), and the upper surface of the second electrode 34.

In some embodiments, a boundary of the graphene film 36 is inside a boundary of the second electrode 34. That is, the sides of the graphene film 36 are on the upper surface of the second electrode 34. The sides of the graphene film 36 are spaced apart from an outer side of the second electrode 34, so as to leave a place for electrical connection on the upper surface of the second electrode 34. That is, the upper surface of the second electrode 34 is connected to a position where there is no graphene film 36. Furthermore, the second electrode 34 is substantially square, and the entire graphene film 36 is also substantially square. The sides of the square graphene film 36 are on the upper surface of the square second electrode 34, and the sides of the square graphene film 36 are spaced apart from the outer side of the square second electrode 34.

In some embodiments, as shown in FIG. 12, there are a plurality of first windows 330. That is, the plurality of first windows 330 arranged at intervals are opened on the isolation layer 33. It can be understood that the plurality of first windows 330 may be arranged at even intervals. That is, the intervals between the adjacent first windows 330 are the same. The plurality of first windows 330 may also be arranged at uneven intervals. That is, the intervals between the adjacent first windows 330 are different, which can be determined by those skilled in the art according to actual conditions.

Furthermore, there are a plurality of second electrodes 34. One second electrode 34 is correspondingly disposed at each first window 330. The plurality of first windows 330 are evenly spaced, and the plurality of second electrodes 34 are evenly spaced accordingly. If the plurality of first windows 330 are arranged at uneven intervals, the plurality of second electrodes 34 are arranged at uneven intervals accordingly. It can be understood that, if the plurality of first windows 330 form an array and each first window 330 corresponds to one graphene film 36, then the plurality of graphene films 36 form an array accordingly. The array graphene film 36 can be prepared with the periodic nanostructures 361 of different periods, duty ratios and/or shapes, which can absorb different characteristic infrared wavelengths to detect a variety of specific gases.

For example, as shown in FIG. 12, four first windows 330 are opened on the isolation layer 33. The four first windows 330 form a square array and are respectively a top left first window, a top right first window, a bottom left first window and a bottom right first window. The top left first window and the top right first window are spaced apart and arranged relative to each other. The top left first window and the bottom left first window are spaced apart and arranged relative to each other. The top right first window and the bottom left first window are spaced apart and arranged relative to each other. The top right first window and the bottom right first window are spaced apart and arranged oppositely. The periodic nanostructures 361 at the top left first window include four circular hole-like structures distributed in an array, and the circular hole-like structure has a first diameter. The periodic nanostructures 361 at the top right first window include nine circular hole-like structures distributed in an array, and the circular hole-like structure has a second diameter. The periodic nanostructures 361 at the bottom left first window include four circular hole-like structures distributed in an array, and the circular hole-like structure has a third diameter. The periodic nanostructures 361 at the bottom right first window include nine circular hole-like structures distributed in an array, and the circular hole-like structure has a fourth diameter. The first diameter is greater than the second diameter, the second diameter is greater than the third diameter, and the third diameter is equal to the fourth diameter.

Furthermore, the graphene film 36 has a single layer or multiple layers. With the multilayer graphene film 36, the absorption peak produces a blue shift and is close to the infrared light band, which is beneficial to the detection of infrared gas and increases the absorption of the characteristic wavelength at the same time.

In some embodiments, the graphene film 36 is a doped graphene film or a composite graphene film. In other words, chemical potential of the graphene film 36 can be changed by doping the graphene film 36 or using the composite graphene film. Alternatively, the graphene film 36 is doped by a chemical doping method. For example, when the graphene film 36 is doped with an oxidizing or reducing gas, the chemical potential of the graphene film 36 can be increased and the characteristic absorption peak is in the near-infrared light band, which is convenient for gas detection.

An infrared sensor according to another embodiment of the present application is described below with reference to FIGS. 13 to 14.

Figure 13:
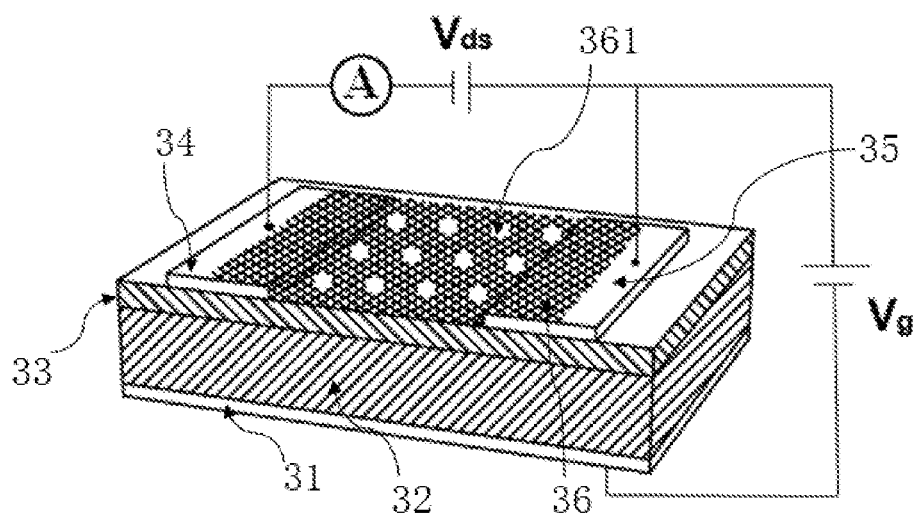
FIG. 13 is a cross-sectional view of an infrared sensor according to another embodiment of the application.
Figure 14:
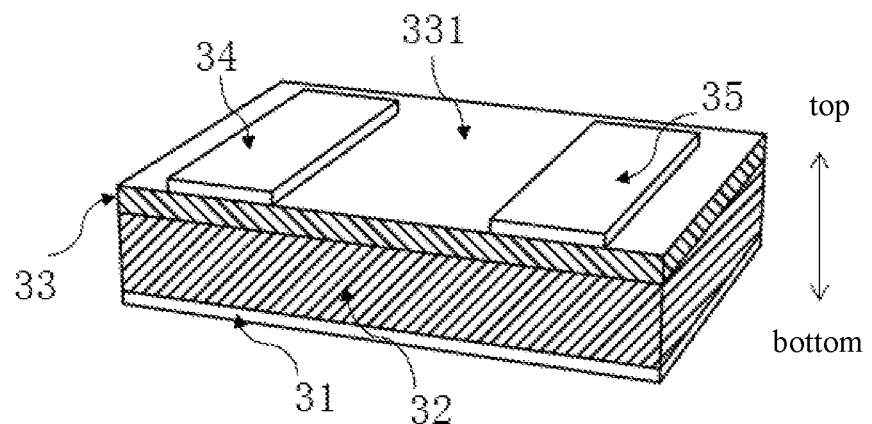
FIG. 14 is a top view of the infrared sensor uncovered with a graphene film according to another embodiment of the application.

As shown in FIGS. 13 and 14, the infrared sensor 3 according to the embodiment of the application includes a first electrode 31, a substrate 32, an isolation layer 33, a second electrode 34, a third electrode 35 and a graphene film 36. The substrate 32 is provided on an upper surface of the first electrode 31. Specifically, a material of the substrate 32 is generally silicon in the art, that is, a silicon substrate. Specifically, the silicon substrate includes an N-type or P-type silicon material with a resistivity less than 0.01 Ω·cm. The substrate 32 in the art can also be made of narrow band gap semiconductor materials such as germanium or gallium arsenide. The isolation layer 33 is provided on an upper surface of the substrate 32. Specifically, the isolation layer 33 is a silica isolation layer, and the thickness of the silica isolation layer is 100 nm to 1000 nm. However, the present application is not limited to this, and the material of the isolation layer 33 can be selected by those skilled in the art according to actual needs.

The second electrode 34 and the third electrode 35 are provided on an upper surface of the isolation layer 33 and spaced apart from each other. In other words, the second electrode 34 and the third electrode 35 are arranged side by side and spaced apart on the upper surface of the isolation layer 33. Alternatively, part of the upper surface of the isolation layer 33 is exposed between the second electrode 34 and the third electrode 35. The exposed upper surface is referred to as a partial upper surface 331 of the isolation layer 33. Furthermore, a side surface of the second electrode 34 opposite to the third electrode 35 is a second inner side surface of the second electrode 34. A side surface of the third electrode 35 opposite to the second electrode 34 is an inner side surface of the third electrode 35. It can be understood that a gap between the second electrode 34 and the third electrode 35 is surrounded by the second inner side surface of the second electrode 34, part of the upper surface 331 of the isolation layer 33, and the inner side surface 51 of the third electrode 35. More specifically, as shown in FIG. 13, the second electrode 34 and the third electrode 35 are spaced apart along a left-to-right direction, in which the second electrode 34 is located at a left side and the third electrode 35 is located at a right side. The left side of the second electrode 34 is located on a right side of the left side of the isolation layer 33. The right side of the third electrode 35 is located on a left side of the right side of the isolation layer 33. The right side of the second electrode 34 is the second inner side of the second electrode 34, and the left side of the third electrode 35 is the inner side of the third electrode 35.

The graphene film 36 is covered on a part of the upper surface 331 of the isolation layer 33 (that is, the upper surface between the second electrode 34 and the third electrode 35), an inner side of the second electrode 34 opposite to the third electrode 35, an inner side surface of the third electrode 35 opposite to the second electrode 34, at least part of the upper surface of the second electrode 34 and at least part of the upper surface of the third electrode 35. In other words, as shown in FIG. 13, the graphene film 36 is arranged corresponding to a gap between the second electrode 34 and the third electrode 35. The graphene film 36 is attached to the upper surface of the second electrode 34, the right side of the second electrode 34, part of the upper surface 331 of the isolation layer 33, the left side of the third electrode 35, and the upper surface of the third electrode 35 in sequence along a left-to-right direction. More specifically, the length of the graphene film 36 along the left-to-right direction is greater than the gap between the second electrode 34 and the third electrode 35, so that the left boundary of the graphene film 36 is located on the upper surface of the second electrode 34, and the right boundary of the graphene film 36 is located on the upper surface of the third electrode 35.

It can be understood that the graphene film 36 is not only a filter capable of absorbing characteristic wavelengths, but also an active film. Because graphene has metallic properties, it can be combined with silicon dioxide/silicon substrate to form a field-effect transistor photodetector. The photo-generated carriers generated by the characteristic infrared light waves absorbed by the graphene film 36 are quickly separated by the electric field between a source electrode and a drain electrode to form a photo-generated current. The infrared sensor according to the embodiment of the present application has advantages of fast response time and not being affected by external heat sources.

The graphene film 36 on a part of the upper surface 331 of the isolation layer 33 has periodic nanostructures 361. In other words, the part of the graphene film 36 on the part of the upper surface 331 of the isolation layer 33 has the periodic nanostructures 361. Specifically, the periodic nanostructures 361 are a plurality of hole-shaped structures, and a cross-section of the hole-shaped structure is a circle or a polygon such as a square, a rhombus or a triangle. For example, as shown in FIG. 13, the cross-section of the hole-like structure is polygonal. The cross-sectional shape of the hole-shaped structure is not limited to this in this application, and those skilled in the art can make a selection according to actual needs.

It can be understood that the present application is not limited to this. For example, the periodic nanostructures 361 include a plurality of doping treatment structures. In other words, the graphene film 36 is doped to obtain the periodic nanostructures.

It is understandable that the infrared sensor uses the graphene film 36 with the periodic nanostructures 361 as a filter, which can enhance the absorption of infrared light and only absorb specific infrared wavelengths to detect specific gases. Therefore, the selection performance of the detector is improved, the volume of the infrared sensor can be reduced, and the preparation and cost are easy.

Furthermore, the first electrode 31, the substrate 32 and the isolation layer 33 are arranged in sequence along a bottom-to-top direction. The upper surface of the isolation layer 33 is provided with a second electrode 34 and a third electrode 35 arranged side by side and spaced apart from each other. It can be understood that in the art, the first electrode 31 is generally referred to as a bottom electrode, and can form an ohmic contact with the substrate 32. The first electrode 31 is a metal thin film electrode, and its metal material is gallium indium alloy, titanium alloy or aluminum. The second electrode 34 is called a source electrode, and the third electrode 35 is called a drain electrode. The second electrode 34 and the third electrode 35 are also metal thin film electrodes, and the metal material is aluminum, gold, or gold-chromium alloy.

In some embodiments, the graphene film 36 includes a first edge and a second edge which are opposite to each other. The second electrode 34 includes a first side away from the third electrode 35. The third electrode 35 includes a second side away from the second electrode 34. The first edge is located inside the first side, and the second edge is located inside the second side, so that the coverage area of the graphene film 36 on the upper surface of the second electrode 34 is smaller than the area of the upper surface of the second electrode 34, and the area covered by the graphene film 36 on the upper surface of the third electrode 35 is smaller than the area of the upper surface of the third electrode 35. As shown in FIG. 14, the left boundary of the graphene film 36 is on the right side of the left boundary of the second electrode 34. That is, the left side of the graphene film 36 is on the upper surface of the second electrode 34. The left side of the graphene film 36 is spaced apart from the left side of the second electrode 34, so as to leave an electrical connection position on the upper surface of the second electrode 34. That is, an electrical connection position on the upper surface of the third electrode 35 is where the graphene film 36 is not present. The right boundary of the graphene film 36 is on the left side of the right boundary of the third electrode 35. The right side of the graphene film 36 is on the upper surface of the third electrode 35, and the right side of the graphene film 36 is spaced from the right side of the third electrode 35, so as to leave an electrical connection position on the upper surface of the third electrode 35. That is, an electrical connection position on the upper surface of the third electrode 35 is where the graphene film 36 is not present.

In some embodiments, the graphene film 36 has a single layer or multiple layers. With the multilayer graphene film 36, the absorption peak produces a blue shift and is close to the infrared light band, which is beneficial to the detection of infrared gas and at the same time increases the absorption of the characteristic wavelength.

In some embodiments, the third electrode 35 and the second electrode 34 are electrically connected, and the first electrode 31 and the third electrode 35 are electrically connected. Alternatively, a voltage between the third electrode 35 and the first electrode 31 is adjustable. The infrared sensor can change a chemical potential of the graphene film 36 by adjusting the voltage between the third electrode 35 and the first electrode 31. Specifically, by adjusting the voltage between the third electrode 35 and the first electrode 31 to dope the graphene film 36, the chemical potential of the graphene film 36 can be increased, and the characteristic absorption peak is in the near-infrared light band, which facilitates gas detection. Moreover, by adjusting the voltage between the third electrode 35 and the first electrode 31, detection of different specific gases can be realized, so that a variety of specific gases can be detected by the infrared sensor.

It is understandable that the above infrared gas detector can be used in various gas detection occasions. For example, it can be applied to air quality detection, air quality monitoring, smart security, and detection of carbon dioxide concentration in a vehicle.

An in-vehicle air quality detection device according to an embodiment of the present application will be described with reference to FIGS. 15 to 16.

The in-vehicle air quality detection device according to the embodiment of the present application includes the infrared gas detector 100, a first processor 200 and a display 300.

The infrared gas detector 100 of the embodiment of the present application can detect gas. The first processor 200 is communicatively connected with the infrared gas detector 100 to receive and process the gas concentration information sent by the infrared gas detector 100. The display 300 is communicatively connected with the processor 200 to receive a display signal sent by the first processor 200 and display concentration information in real time. Specifically, when the infrared gas detector 100 detects the gas concentration, the first processor 200 receives the gas concentration value sent by the infrared gas detector 100, analyzes the gas concentration value, and sends it to the display 300. The display 300 can display the gas concentration and the air quality analysis value in real time.

Figure 16:
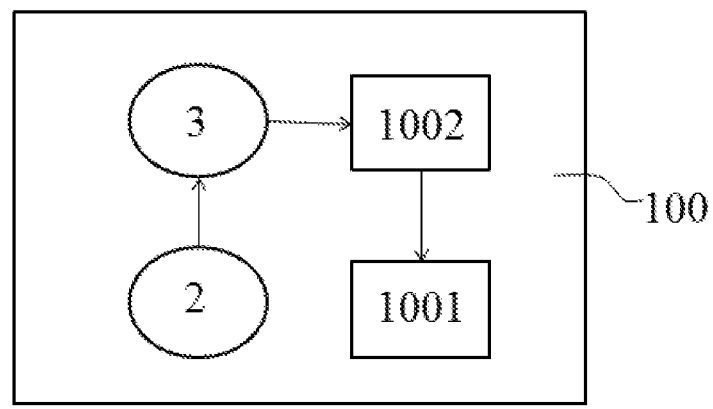
FIG. 16 is a schematic structural view of an infrared gas detector according to an embodiment of the present application.

In some embodiments, as shown in FIG. 16, the infrared gas detector 100 further includes a second processor 1001. The second processor 1001 is communicatively connected with the infrared sensor 3 to receive and process the voltage signal sent by the infrared sensor 3.

In some embodiments, as shown in FIG. 16, the infrared gas detector 100 further includes a signal processing circuit 1002. The signal processing circuit 1002 is communicatively connected with the infrared sensor 3 and the second processor 1001 to perform filtering, amplification, temperature compensation and digital-to-analog conversion on the voltage signal sent by the infrared sensor 3.

Figure 15:
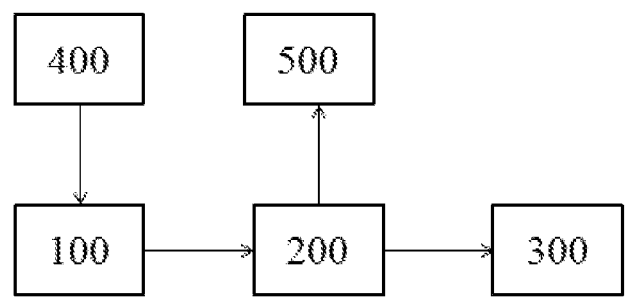
FIG. 15 is a schematic structural view of an in-vehicle air quality monitoring device according to an embodiment of the present application.

In some embodiments, as shown in FIG. 15, the in-vehicle air quality monitoring device further includes a voltage conversion module 400. The voltage conversion module 400 is communicatively connected with the infrared gas detector 100 to convert an external voltage into a working voltage of the infrared gas detector 100.

In some embodiments, as shown in FIG. 15, the in-vehicle air quality monitoring device further includes a warning device 500. The warning device 500 is in communication with the first processor 200 to raise an alarm. It is understandable that when the first processor 200 finds that the gas concentration exceeds a standard during analysis and processing, the first processor 200 will send a warning signal to the warning device 500 to make the warning device 500 raise an alarm to remind a user that the gas concentration exceeds the standard. Alternatively, the warning device 500 may be a sound reminder, a vibration reminder, or a light-emitting reminder, such as a buzzer, a flashlight, and the like. It can be understood that the application is not limited to this.

The air quality monitoring device according to the embodiment of the present application will be described below with reference to FIGS. 16 to 17.

The air quality monitoring device according to the embodiment of the present application includes the infrared gas detector 100 according to the embodiment of the present application, the first processor 200, the display 300 and a control switch 900. The infrared gas detector 100 according to the embodiment of the present application can detect gas, for example, the characteristic wavelength of the gas to be detected is 3.4 to 4.7 μm. The first processor 200 is communicatively connected with the control switch 900, and the control switch 900 can provide a control signal to the first processor 200. The first processor 200 is communicatively connected with the infrared gas detector 100. The first processor 200 can activate the infrared gas detector 100 according to the control signal provided by the control switch 900, and receive and process the gas concentration information sent by the infrared gas detector 100. The display 300 is communicatively connected with the first processor 200 to receive the display signal sent by the first processor 200 and display the gas concentration value in real time. Specifically, when the infrared gas detector 100 detects the gas concentration, the first processor 200 receives the gas concentration value sent by the infrared gas detector 100, analyzes the gas concentration value, and sends it to the display 300. The display 300 can display the gas concentration and the air quality analysis value in real time.

In some embodiments, the air quality monitoring device according to the embodiments of the present application may use the infrared gas detector of the specific embodiment shown in FIGS. 10 to 12.

As shown in FIG. 12, there are a plurality of first windows 330, and each first window 330 is provided with one graphene film 36 accordingly. The periodic nanostructures 361 on each of the graphene films 36 are different. A Schottky junction with the periodic nanostructures 361 can absorb a characteristic infrared wavelength to detect a specific gas. Therefore, a plurality of diodes with the Schottky junction composed of the above structure can absorb different characteristic infrared wavelengths to detect a variety of specific gases. The different periodic nanostructures 361 may be that the multiple periodic nanostructures 361 have different periods, duty cycles, and/or shapes. Alternatively, the plurality of first windows 330 form an array, and the plurality of graphene films 36 form an array accordingly. The periodic nanostructures 361 with different periods, duty cycles and/or shapes can be prepared on the array graphene film 36 to detect a variety of specific gases.

Figure 17:
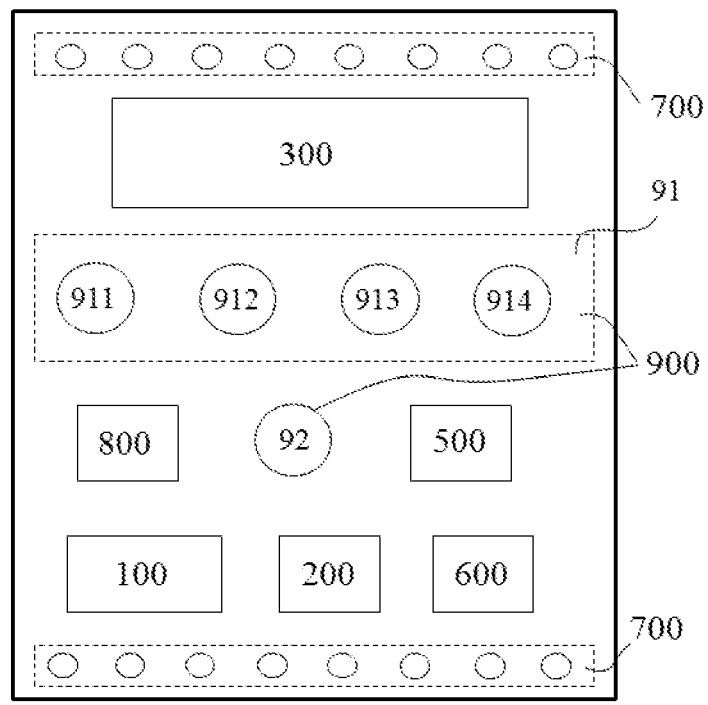
FIG. 17 is a schematic structural view of the air quality monitoring device according to an embodiment of the present application.

Thus, as shown in FIG. 17, when the first processor 200 controls the infrared gas detector 100, the first processor 200 can send different control information to the infrared gas detector 100 according to different control signals provided by the control switch 900, in order to activate the second electrode 34 corresponding to the different periodic nanostructures 361. As a result, the diodes with the Schottky junction formed at the corresponding positions of the different periodic nanostructures 361 work separately to detect different gases.

It is understandable that the infrared detector uses the graphene film 36 with the periodic nanostructures 361 as a filter, which can enhance the absorption of infrared light and only absorb specific infrared wavelengths to detect specific gases. Therefore, the selection performance of the detector is improved, the volume of the infrared sensor can be reduced, and the preparation and cost are easy.

According to the air quality monitoring device of the embodiment of the present application, by arranging the infrared detector with different periodic nanostructures, it can detect a variety of different gases to realize multifunctional air quality detection. Since the detection of multiple different gases can be completed by one infrared detector, the volume of the air quality monitoring device can be reduced and the space occupied is small.

In some specific embodiments, the control switch 900 includes a plurality of selection buttons 91. The plurality of selection buttons 91 are in a one-to-one correspondence to the plurality of second electrodes 34. That is, each selection button 91 corresponds to one second electrode 34.

Specifically, after activating one of the selection buttons 91, the first processor 200 sends a voltage control signal, and the first processor 200 receives the voltage control signal and sends a signal to the infrared sensor 3 to activate a second electrode 34. Therefore, the diode with the Schottky junction corresponding to the second electrode 34 works to detect a specific gas. By controlling different selection buttons 91, a plurality of second electrodes 34 can be activated respectively to detect a plurality of different gases. For example, as shown in FIGS. 12 and 17, there are four selection buttons 91, and the four selection buttons 91 are a first gas button 911, a second gas button 912, a third gas button 913 and a fourth gas button 914, respectively. There are also four first windows 330, four second electrodes 34 and four graphene films 36. The four selection buttons 91 respectively correspond to the first windows 330 and the second electrodes 34 and the graphene films 36 corresponding to the first windows 330. A first gas, a second gas, a third gas and a fourth gas can be detected respectively by controlling the four selection buttons 91, respectively.

It can be understood that the control method of the plurality of second electrodes 34 is not limited to this. In other alternative embodiments, the control switch 900 includes an automatic detection button 92, and the automatic detection button 92 corresponds to the plurality of second electrodes 34. In other words, the automatic detection button 92 can send a control signal to the first processor 200 so that the first processor 200 can control different second electrodes 34 respectively. Specifically, after the automatic detection button 92 is activated, the first processor 200 receives the control signal of the automatic detection button 92, and sends different information to the infrared gas detector 100 at specific time intervals to activate different second electrodes 34, thereby detecting different gases, and continuously performing cycle detection.

In some other embodiments, the air quality monitoring device according to the embodiments of the present application may use the infrared gas detector of the specific embodiment shown in FIGS. 13 to 14.

As shown in FIG. 13, a voltage is applied between the third electrode 35 and the first electrode 31 and the voltage between the third electrode 35 and the first electrode 31 is adjustable. Among them, the control switch 900 controls and adjusts the voltage of the third electrode 35. By adjusting the voltage between the third electrode 35 and the first electrode 31, the chemical potential of the graphene film 36 can be changed, and the detection of different specific gases can be realized, so that the infrared sensor 3 detects a variety of different gases.

According to the in-vehicle air quality monitoring device of the embodiment of the present application, a variety of different gases can be detected by setting an infrared detector with an adjustable voltage to realize multifunctional air quality detection. On account of the detection of a variety of different gases can be completed by one infrared detector, the volume of the in-vehicle air quality monitoring device can be reduced and the space occupied is small.

In some specific embodiments, as shown in FIG. 17, the control switch 900 includes a plurality of selection buttons 91, and voltages between the third electrode 35 and the first electrode 31 controlled by the plurality of selection buttons 91 are different.

Specifically, after one of the plurality of selection buttons 91 is activated, a voltage control signal is sent to the first processor 200. The first processor 200 receives the voltage control signal and sends a signal to the infrared sensor 3, and provides a voltage to the third electrode 35, so that the infrared sensor 3 detects a specific gas. Thus, by controlling different selection buttons 91, different voltages can be applied to the third electrode 35, thereby detecting a variety of different gases. For example, as shown in FIG. 17, there are four selection buttons 91 which are a first gas button 911, a second gas button 912, a third gas button 913 and a fourth gas button 914, respectively. The four selection buttons 91 enable four different voltages to be applied between the third electrode 35 and the first electrode 31 to detect a first gas, a second gas, a third gas and a fourth gas, respectively.

It can be understood that the control method between the third electrode 35 and the first electrode 31 is not limited to this. In other alternative embodiments, the control switch 900 includes an automatic detection button 92, which can control the third electrode 35 and the first electrode 31 to have different voltages. In other words, the automatic detection button 92 can send a control signal to the first processor 200 so that the first processor 200 controls and applies different voltages between the third electrode 35 and the first electrode 31. Specifically, after the automatic detection button 92 is activated, the first processor 200 receives the control signal of the automatic detection button 92 and sends different information to the infrared gas detector 100 at specific intervals. Different voltages are applied between the third electrode 35 and the first electrode 31 so as to detect different gases and continuously perform cycle detection.

In some embodiments, as shown in FIG. 16, the infrared gas detector 100 further includes a second processor 1001. The second processor 1001 is communicatively connected with the infrared sensor 3 to receive and process the voltage signal sent by the infrared sensor 3.

In some embodiments, as shown in FIG. 16, the infrared gas detector 100 further includes a signal processing circuit 1002. The signal processing circuit 1002 is communicatively connected with the infrared sensor 3 and the second processor 1001 to perform filtering, amplification, temperature compensation and digital-to-analog conversion on the voltage signal sent by the infrared sensor 3.

In some embodiments, as shown in FIG. 17, the air quality monitoring device further includes a warning device 500 which is communicatively connected with the first processor 200 to raise an alarm. It is understandable that when the first processor 200 finds that the gas concentration exceeds a standard during analysis and processing, the first processor 200 will send a warning signal to the warning device 500 to make the warning device 500 raise an alarm to remind the user that the gas concentration exceeds the standard. Wherein, a specific alarm mode can be referred to the above-mentioned embodiment.

In some embodiments, the air quality monitoring device further includes a fan 600. The fan 600 can be a fan with low power consumption and low noise. The fan 600 can speed up the control of air circulation in the quality monitoring device.

It is understandable that the air quality monitoring device is provided with air holes 700 to facilitate the detection of external air entering the air quality monitoring device, or to discharge the internal air in time. Alternatively, a plurality of air holes 700 are respectively provided on the upper and lower parts of the air quality monitoring device. In addition, the air quality monitoring device further includes a power supply 800 to supply power to the air quality monitoring device.

Figure 18:
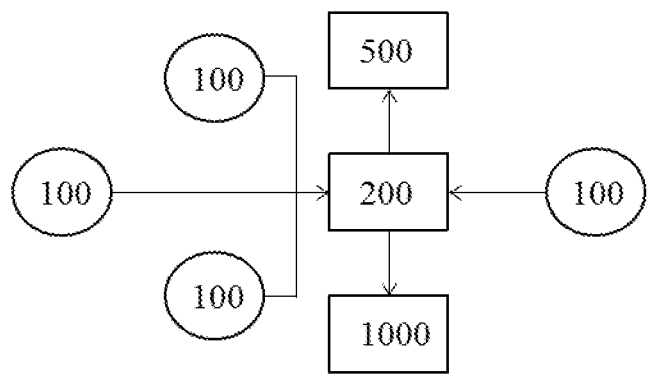
FIG. 18 is a schematic structural view of an intelligent security device according to an embodiment of the present application.

The intelligent security device according to an embodiment of the present application will be described below with reference to FIGS. 16 and 18.

The intelligent security device according to the embodiment of the present application includes an infrared gas detector 100, a first processor 200, a fire extinguisher 1000 and a warning device 500.

There are a plurality of infrared gas detectors 100 of which some can detect flames, and others can detect gas. Specifically, the characteristic wavelength of the flame is 4.4 µm, the gas to be detected is a hydrocarbon refrigerant gas, and the characteristic wavelength of the hydrocarbon refrigerant gas is 3.33 to 3.46 µm. For example, the characteristic wavelength of propane is 3.4 µm. The first processor 200 is communicatively connected with the infrared gas detector 100 to receive and process the output signal of the infrared gas detector 100 and output control signals. The fire extinguisher 1000 is communicatively connected with the first processor 200 to receive the fire extinguishing control signal sent by the first processor 200 when some of the infrared gas detectors 100 detect a flame, and spray fire extinguishing materials to the position of the flame. The warning device 500 is communicatively connected with the first processor 200 to receive the warning control signal sent by the first processor 200 and raise an alarm.

It is understandable that when the first processor 200 receives a flame information detected by some infrared gas detectors 100, after analysis and processing, it sends a warning signal to the warning device 500 so that the warning device 500 raises an alarm to remind the user that there is a flame. When the first processor 200 receives a leaked gas information detected by some other infrared gas detectors 100, after analysis and processing, it sends a warning signal to the warning device 500 so that the warning device 500 raises an alarm to remind the user that there is a flammable gas leak. Wherein, the specific alarm mode can be referred to the above-mentioned embodiment.

Specifically, the intelligent security device according to the embodiment of the present application adopts the infrared gas detector 100 of the specific embodiment shown in FIGS. 13 to 14.

No voltage is applied between the third electrode 35 and the first electrode 31 of some infrared gas detectors 100 among the infrared gas detectors 100 to detect flames. Specifically, the graphene film 36 in the infrared gas detector 100 has periodic nanostructures 361 on it. The periodic nanostructures 361 only absorb flame infrared characteristic light with a specific wavelength. It is not necessary to apply a voltage between the third electrode 35 and the first electrode 31 of the infrared gas detector 100 to realize flame detection.

Some other infrared gas detectors 100 among the infrared gas detectors 100 have a voltage applied between the third electrode 35 and the first electrode 31 of the infrared gas detector 100 and the voltage is adjustable. The chemical potential of the graphene film 36 of the infrared gas detector 100 can be changed by adjusting the voltage between the third electrode 35 and the first electrode 31 of the infrared gas detector 100. In this way, the infrared gas detector 100 can detect different specific gases, so that the infrared sensor 3 of the infrared gas detector 100 detects a variety of different gases.

According to the intelligent security device of the embodiment of the present application, a plurality of infrared gas detectors are provided, and a voltage is applied between the third electrode 35 and the second electrode 34 on some infrared gas detector to detect the flame, and a voltage is applied between the third electrode 35 and the first electrode 31 on some other infrared gas detectors and the voltage is adjustable to detect a variety of different gases, thereby simultaneously detecting gases and flames. Compared with the existing assembly of sensors of different structural forms, the intelligent security device assembles sensors of the same structural form together, so that the cost can be reduced.

In some embodiments, there are some infrared gas detectors 100 which are set in different directions to detect flames in different directions. It is understandable that by arranging the infrared gas detector 100 capable of detecting flames in different directions, flame detection can be performed in each direction, so as to improve the efficiency of flame detection. Specifically, the intelligent security device based on the graphene infrared detector also includes a control board. The infrared gas detectors 100 are respectively arranged on front, left and right sides of the control board to monitor whether there are fire sources in the three directions. In other words, the infrared gas detectors 100 are respectively provided on the front, left and right sides of the control board. It can be understood that the installation position and direction of the infrared gas detectors 100 are not limited to this, and those skilled in the art can determine according to the actual situation.

In some embodiments, the infrared gas detector 100 further includes a second processor 1001, and the second processor 1001 is communicatively connected with the infrared sensor 3 to receive and process the voltage signal sent by the infrared sensor 3.

In some embodiments, the infrared gas detector 100 further includes a signal processing circuit 1002. The signal processing circuit 1002 is communicatively connected with the infrared sensor 3 to perform filtering, amplification, temperature compensation and digital-to-analog conversion on the voltage signal generated by the infrared sensor 3.

In some embodiments, the fire extinguisher 1000 includes a motor and a spray assembly. The motor drives the spray assembly to be positioned according to the orientation of the flame detected by the graphene infrared detector to spray the fire extinguishing material to the flame. Specifically, the spray assembly can be rotated and positioned so that it is aimed at the flame. In addition, the fire extinguishing material may be dry ice.

Further, the first processor 200 can control the spray range of the fire extinguisher 1000 according to the position of the flame detected by the infrared sensor 3.

Hereinafter, a method for detecting the concentration of carbon dioxide in a vehicle according to an embodiment of the present application will be described with reference to FIGS. 16 and 19.

Figure 19:
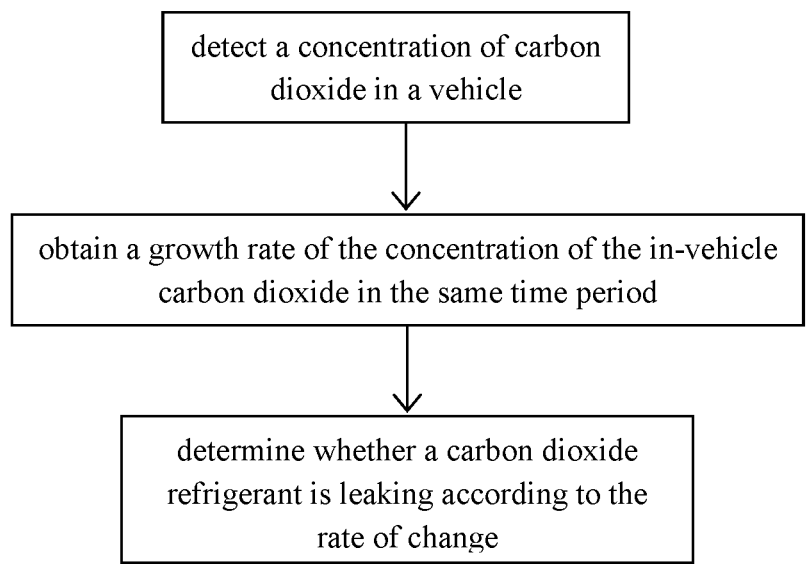
FIG. 19 is a flowchart of a method for detecting carbon dioxide concentration in a vehicle according to an embodiment of the present application.

As shown in FIG. 19, according to the method for detecting carbon dioxide concentration in a vehicle according to an embodiment of the present application, the vehicle is equipped with an air conditioning system with carbon dioxide refrigerant, and the method for detecting carbon dioxide concentration in the vehicle includes the following steps:

detect the concentration of carbon dioxide in the vehicle:

It is understandable that a gas infrared sensor 100 may be provided on the vehicle to detect the concentration of carbon dioxide in the vehicle. Specifically, the gas infrared sensor 100 is arranged at an air outlet of the air conditioning system to detect the concentration of carbon dioxide at the air outlet of the air conditioning system. Setting the gas infrared sensor 100 at the air outlet of the air conditioning system can facilitate the air circulation inside the gas sensor, improve the response of the gas infrared sensor 100, and quickly detect the concentration of carbon dioxide in the vehicle.

obtain a growth rate of the concentration of carbon dioxide in the same time period, where the growth rate has a first preset growth rate and a second preset growth rate greater than the first preset growth rate:

It is understandable that the "same time period" in the growth rate of the carbon dioxide concentration in the same time period can be determined according to actual conditions. For example, the same time period can be one second, that is, the growth rate of the concentration of carbon dioxide in the first one second, the growth rate in the next one second, the growth rate in the following one second etc., to obtain the concentration of carbon dioxide in each one second rate of growth. The same time period can also be 2 seconds, that is, the growth rate of the concentration of carbon dioxide in every 2 seconds is obtained. Specifically, in the two preset growth rates of the concentration of carbon dioxide, one of which is a first preset growth rate, the other is a second preset growth rate, and the second preset growth rate is much greater than the first preset growth rate. In other words, when the growth rate of the concentration of carbon dioxide is less than or equal to the first preset growth rate, it means that the concentration of carbon dioxide increases slowly in the same time period. When the increase in the concentration of carbon dioxide is greater than or equal to the second preset growth rate, it means that the concentration of carbon dioxide increases faster in the same time period. It is understandable that the specific values of the first preset growth rate and the second preset growth rate can be determined by those skilled in the art according to actual conditions.

determine the source of carbon dioxide:

When the growth rate of the concentration of carbon dioxide is less than or equal to the first preset growth rate, the source of carbon dioxide is carbon dioxide exhaled by the human body. When the growth rate of the concentration of carbon dioxide is greater than or equal to the second preset growth rate, the source of the carbon dioxide is the leakage of the carbon dioxide refrigerant of the air conditioning system. In other words, when the concentration of carbon dioxide increases slowly, the main source of carbon dioxide is carbon dioxide exhaled by the human body. When the concentration of carbon dioxide increases rapidly, the main source of carbon dioxide is the leakage of carbon dioxide refrigerant from the air conditioning system. Since carbon dioxide is produced during human breathing, inside the vehicle is a closed environment, and the concentration of carbon dioxide will increase within a certain period of time. But if it is mainly carbon dioxide exhaled by the human body, the increase of the concentration of carbon dioxide will be slower. However, if the carbon dioxide refrigerant in the air-conditioning system leaks, which increases the concentration of carbon dioxide in the vehicle, the increase in the concentration of carbon dioxide will be faster.

According to the method for detecting the concentration of carbon dioxide in the vehicle according to the embodiment of the present application, the concentration of carbon dioxide in the vehicle can be detected, and the main source of carbon dioxide can be accurately judged according to the growth rate of the carbon dioxide concentration, so as to accurately determine whether the carbon dioxide refrigerant in the air conditioning system of the vehicle is leaking or not. By knowing whether the carbon dioxide refrigerant is leaking or not, it is possible to avoid harm to the human body, and at the same time to know whether the refrigeration of the air conditioning system is working normally.

In some embodiments, the air conditioning system has an external circulation and an inner circulation. The concentration of carbon dioxide has a first preset concentration and a second preset concentration smaller than the first preset concentration. The method for detecting the concentration of carbon dioxide in a vehicle according to the embodiment of the present application further includes that when the concentration of carbon dioxide exceeds the first preset concentration, the external circulation is turned on.

In other words, there are two preset concentrations of carbon dioxide in the vehicle, one is the first preset concentration, the other is the second preset concentration, and the second preset concentration is much smaller than the first preset concentration. For example, the first preset concentration is 1500 ppm, and the second preset concentration is 500 ppm. When the concentration of carbon dioxide in the vehicle exceeds the first preset concentration, the concentration of carbon dioxide in the vehicle exceeds the standard, and the air environment in the vehicle is dirty, which easily causes breathing difficulties for the human body and endangers human health. When the concentration of carbon dioxide in the vehicle is lower than the second preset concentration, the concentration of carbon dioxide in the vehicle is normal, the air in the vehicle is good, and the human body breathes smoothly. It can be found that when the concentration of carbon dioxide in the vehicle exceeds the first preset concentration, the external circulation of the air conditioning system needs to be turned on for ventilation. That is, a fan is used to make the outside air enter the vehicle, and the air inside the vehicle is discharged to the outside of the vehicle by the fan.

Further, the method for detecting the concentration of carbon dioxide in the vehicle further includes: when the concentration of carbon dioxide is lower than the second preset concentration, the external circulation is turned off and the inner circulation is turned on. It is understandable that when the concentration of carbon dioxide in the vehicle is lower than the second preset concentration, the concentration of carbon dioxide in the vehicle is normal, the air is good, and the human body breathes smoothly. The external circulation of the air conditioning system can be turned off and the inner circulation can be turned on to reduce the energy consumption of the vehicle. It is understandable that the inner circulation uses the existing air in the vehicle to circulate, which means the outside air is not allowed to enter the vehicle.

In some embodiments, the method for detecting the concentration of carbon dioxide in the vehicle further includes: determining that the source of the carbon dioxide is the leakage of the carbon dioxide refrigerant and closing the inner circulation and issuing an alarm. It is understandable that when it is detected that the main source of carbon dioxide in the vehicle is the leakage of carbon dioxide refrigerant, the air conditioning system should be turned off and an alarm should be issued in time to remind users to open windows for ventilation and avoid harm to the human body.

In some embodiments, as shown in FIG. 15, the detected carbon dioxide information is received and processed by the first processor 200, and the growth rate of the concentration of carbon dioxide in the same time period is obtained to determine the main source of carbon dioxide. In other words, the first processor 200 is communicatively connected with the gas infrared sensor 100, and the first processor 200 receives the information sent by the gas infrared sensor 100 and performs analysis and processing, so as to obtain the growth rate of the carbon dioxide concentration in the same time period and determine the main source of carbon dioxide in the vehicle according to the growth rate.

In some embodiments, as shown in FIG. 15, the first processor 200 is communicatively connected with a display 300 and a warning device 500. The display 300 can display the concentration and growth rate of carbon dioxide. The warning device 500 can raise an alarm. Specifically, the first processor 200 is communicatively connected with the display 300 and also communicatively connected with the warning device 500. The display 300 can receive the display signal sent by the first processor 200 to display information such as the concentration of carbon dioxide and the growth rate of the concentration. The warning device 500 can receive the warning signal sent by the first processor 200 to raise an alarm, so as to alert the user when the carbon dioxide refrigerant leaks or the carbon dioxide concentration in the vehicle exceeds the standard. Among them, the specific alarm mode can be referred to the above-mentioned embodiment.

In some embodiments, the gas infrared sensor 100 is communicatively connected to a voltage conversion module 400, and the voltage conversion module 400 can convert an external voltage into a working voltage of the infrared gas infrared sensor 100.

In some embodiments, the gas sensor for detecting the carbon dioxide concentration 100 is an infrared gas detector which includes an infrared detector and an infrared light source. The infrared light source is used to emit infrared light to the infrared detector. Specifically, the infrared light source 102 may be infrared light generated by heating and luminescence of a filament, or may be an infrared LED light source. It can be understood that the configuration of the infrared light source 102 is not limited to this in this application.

In the description of this specification, descriptions with reference to the terms "an embodiment", "some embodiments", "examples", "specific embodiments", or "some examples" etc., mean that the specific feature, structure, material or feature described in conjunction with the embodiment or example is included in at least one embodiment or example of the application. In this specification, the schematic representations of the above terms do not necessarily refer to the same embodiment or example. Moreover, the described specific features, structures, materials, or characteristics can be combined in any one or more embodiments or examples in an appropriate manner. In addition, those skilled in the art can combine and combine the different embodiments or examples and the features of the different embodiments or examples described in this specification without contradicting each other.

Although the embodiments of the application have been shown and described above, it can be understood that the above-mentioned embodiments are exemplary and should not be construed as limiting the application. Those of ordinary skill in the art can make changes, modifications, substitutions and amendments to the above-mentioned embodiments within the scope of the application.

What is claimed is:

1. An infrared sensor comprising:
a first electrode;
a substrate being provided on an upper surface of the first electrode;
an isolation layer being provided on an upper surface of the substrate;
a second electrode being provided on an upper surface of the isolation layer; and
a graphene film being covered on at least a part of the second electrode, and the graphene film having periodic nanostructures, the periodic nanostructures being a plurality of hole-like structures.

2. The infrared sensor according to claim 1, wherein the isolation layer is provided with a first window and a first inner side surface surrounding the first window, and the first window is used to expose part of the upper surface of the substrate; the second electrode is provided with a second window and a second inner side surface surrounding the second window, the first window and the second window are arranged correspondingly; and the graphene film is covered on part of the upper surface of the substrate, the first inner side surface of the isolation layer, the second inner side surface of the second electrode and the upper surface of the second electrode.

3. The infrared sensor according to claim 2, wherein there are a plurality of the first windows which are evenly spaced; there are a plurality of the second electrodes and a plurality of the graphene films; and an outer periphery of each first window is surrounded by one of the second electrodes, and the upper surface of each second electrode is covered with one of the graphene films.

4. The infrared sensor according to claim 1, wherein a cross-section of each hole-like structure is in a shape of a circle, a square, a diamond or a triangle, the graphene film has the periodic nanostructures on a part of the upper surface of the substrate, a projection of the graphene film on a horizontal plane is located within a projection of an outer periphery of the second electrode on the horizontal plane, and the graphene film is a doped graphene film or a composite graphene film.

5. The infrared sensor according to claim 1, further comprising a third electrode provided on the upper surface of the isolation layer, the second electrode and the third electrode being spaced apart from each other, the graphene film being covered on the upper surface of the isolation layer between the second electrode and the third electrode, the inner surface of the second electrode opposite to the third electrode, the inner side of the third electrode opposite to the second electrode, at least part of the upper surface of the second electrode and at least part of the upper surface of the third electrode, the periodic nanostructures being provided on a portion of the graphene film which is on the upper surface of the isolation layer, the graphene film comprising a first edge and a second edge opposite to each other, the second electrode comprising a first side away from the third electrode, the third electrode comprising a second side away from the second electrode, the first edge being located inside the first side, and the second edge being located inside the second side.

6. The infrared sensor according to claim 5, wherein the third electrode and the second electrode are electrically connected.

7. The infrared sensor according to claim 6, wherein chemical potential of the graphene film is changeable by adjusting a voltage between the third electrode and the first electrode so that the infrared sensor is capable of detecting a variety of different gases.

8. An infrared gas detector comprising a housing, an infrared light source and an infrared sensor, the infrared sensor comprising:
a first electrode;
a substrate being provided on an upper surface of the first electrode;
an isolation layer being provided on an upper surface of the substrate;
a second electrode being provided on an upper surface of the isolation layer; and
a graphene film being covered on at least a part of the second electrode, and the graphene film having periodic nanostructures, the periodic nanostructures being a plurality of hole-like structures;
the housing being provided with a through hole, and the housing comprising:
a first housing which has a first chamber communicating with the through hole, an inner surface of a side wall of the first housing being provided with a first reflection surface, a second reflection surface, a third reflection surface and a fourth reflection surface; and
a second housing which is connected to the first housing, the second housing being provided with a first channel and a second channel spaced apart from each other, the first channel being in communication with the first chamber, the second channel being in communication with the first chamber, the infrared light source being arranged in the first channel, the infrared sensor being arranged in the second channel, an infrared light emitted by the infrared light source being transmitted to the first reflection surface along the first channel, and being reflected to the fourth reflection surface sequentially via the first reflection surface, the second reflection surface and the third reflection surface, the infrared light incident on the fourth reflection surface being reflected by the fourth reflection surface and being transmitted to the infrared sensor along the second channel, a plane on which an optical path of the infrared light in the first channel and an optical path in the second channel are located being a first plane, a plane where an optical path of the infrared light is reflected to the fourth reflection surface sequentially via the first reflection surface, the second reflection surface and the third reflection surface being a second plane, and the second plane and the first plane being perpendicular to each other.

9. The infrared gas detector according to claim 8, wherein the side wall of the first housing comprises a first side wall, a second side wall, a third side wall, a fourth side wall, a fifth side wall and a sixth side wall which are connected in sequence and enclose the first chamber, the inner surface of the first side wall being outwardly inclined by 45° along a direction toward the second housing, the second side wall and the sixth side wall being parallel to each other, the third side wall and the fifth side wall being inclined by 45° with respect to the fourth side wall and an angle between the third side wall and the fifth side wall being 90°, the first reflection surface and the fourth reflection surface being provided on an inner surface of the first side wall and spaced apart from each other, the second reflection surface being provided on an inner surface of the third side wall, and the third reflection surface being provided on an inner surface of the fifth side wall.

10. The infrared gas detector according to claim 8, wherein an axial direction of the first channel is parallel to an axial direction of the second channel.

11. The infrared gas detector according to claim 8, wherein the second housing has a second chamber communicating with the first chamber, the through hole being provided on the second housing, the through hole comprising a first through hole and a second through hole, the first through hole communicating with the second chamber, and the second through hole communicating with the second chamber and the first chamber.

12. The infrared gas detector according to claim 11, wherein a side wall of the second housing comprises a second left side wall and a second right side wall spaced apart from the second left side wall, the first through hole is provided on the second left side wall and the second right side wall, a partition is provided in the second chamber which divides the second chamber into a second left chamber and a second right chamber, the first through hole on the second left side wall communicates with the second left chamber, the first through hole on the second right side wall communicates with the second right chamber, and there are a plurality of the first through holes and a plurality of the second through holes.

13. The infrared gas detector according to claim 8, further comprising a reflector cup nested in the first channel and abutting against an inner surface of the first channel, the infrared light source being arranged in the reflector cup;
the reflector cup comprising a cylindrical section and a parabolic section connected to an upper end of the cylindrical section, the first channel comprising a first section, a second section and a third section which are sequentially arranged along a bottom-to-top direction, an outer peripheral profile of the cylindrical section being adapted to an inner peripheral profile of the first section, an outer peripheral profile of the parabolic section being adapted to an inner peripheral profile of the second section, and an inner diameter of the third section being consistent along an axial direction of the first channel.

14. The infrared gas detector according to claim 8, wherein the second housing is provided at the bottom of the first housing, both of the first channel and the second channel being extending downwardly from an upper surface of the second housing to a bottom of the second housing;
the infrared gas detector further comprises a circuit board, a bottom of the second housing being provided with an opening, the circuit board being provided at the bottom of the second housing, and both the infrared light source and the infrared sensor being provided on an upper surface of the circuit board.

15. The infrared gas detector according to claim 8, wherein each of the first reflection surface, the second reflection surface, the third reflection surface and the fourth reflection surface is provided with a coated film to improve reflection of the infrared light.

16. An air quality detection device comprising an infrared gas detector and a first processor, the infrared gas detector comprising a housing, an infrared light source and an infrared sensor, the infrared sensor comprising:

a first electrode;
a substrate being provided on an upper surface of the first electrode;
an isolation layer being provided on an upper surface of the substrate;
a second electrode being provided on an upper surface of the isolation layer; and
a graphene film being covered on at least part of the second electrode, and the graphene film having periodic nanostructures, the periodic nanostructures being a plurality of hole-like structures;
the housing being provided with a through hole, and the housing comprising:
a first housing which has a first chamber communicating with the through hole, an inner surface of a side wall of the first housing being provided with a first reflection surface, a second reflection surface, a third reflection surface and a fourth reflection surface; and
a second housing which is fixed to the first housing, the second housing being provided with a first channel and a second channel spaced apart from each other, the first channel and the second channel being in communication with the first chamber, the infrared light source being arranged in the first channel, the infrared sensor being arranged in the second channel, the infrared light source being capable of emitting an infrared light which is transmitted to the first reflection surface along the first channel, and reflected to the fourth reflection surface sequentially via the first reflection surface, the second reflection surface and the third reflection surface, the infrared light incident on the fourth reflection surface being reflected by the fourth reflection surface so as to be transmitted to the infrared sensor along the second channel; wherein
the first processor is electrically connected with the infrared gas detector to receive and process a gas concentration information sent by the infrared gas detector.

17. The air quality detection device according to claim 16, wherein a cross-section of each hole-like structure is in a shape of a circle, a square, a diamond or a triangle, and the infrared gas detector comprises a second processor electrically connected with the infrared sensor to receive and process a voltage signal sent by the infrared sensor.

18. The air quality detection device according to claim 17, wherein the infrared gas detector comprises a signal processing circuit which is electrically connected with the infrared sensor and the second processor to perform filtering, amplification, temperature compensation and digital-to-analog conversion on the voltage signal sent by the infrared sensor.

19. The air quality detection device according to claim 16, further comprising a voltage conversion module electrically connected with the infrared gas detector to convert an external voltage into a working voltage of the infrared gas detector.

20. The air quality detection device according to claim 16, further comprising a display electrically connected with the first processor to receive a display signal sent by the first processor and display the gas concentration information in real time.

* * * * *